United States Patent [19]

Kyle

[11] Patent Number: 5,538,989
[45] Date of Patent: Jul. 23, 1996

US005538989A

[54] FENBENDAZOLE FORMULATIONS

[75] Inventor: Leslie E. Kyle, Piscataway, N.J.

[73] Assignee: Hoechst-Roussel Agri-Vet Company, Somerville, N.J.

[21] Appl. No.: 149,877

[22] Filed: Nov. 10, 1993

[51] Int. Cl.⁶ .............. A61K 31/415; A61K 31/695; A61K 31/045
[52] U.S. Cl. .............. 514/394; 514/63; 514/395; 514/730; 514/941
[58] Field of Search .................. 514/394, 395, 514/63, 730, 941

[56] References Cited

U.S. PATENT DOCUMENTS

| | | | |
|---|---|---|---|
| 3,897,559 | 7/1975 | Friedman | 424/275 |
| 3,954,791 | 5/1976 | Lowe | 548/309.1 |
| 4,197,307 | 4/1980 | Gallay et al. | 514/394 |

*Primary Examiner*—Kevin E. Weddington
*Attorney, Agent, or Firm*—Barbara V. Maurer

[57] ABSTRACT

This application relates to an aqueous formulation of fenbendazole which is stable and efficacious, does not agglomerate upon standing and wherein the fenbendazole remains in suspension after standing for twenty-four hours.

33 Claims, No Drawings

FENBENDAZOLE FORMULATIONS

This application relates to new and useful formulations of fenbendazole.

Fenbendazole is a benzimidazole carbamate compound used as a veterinary anthelmintic in many species, including poultry, swine and cattle. Fenbendazole is used to control nematodes such as Ascaridia, Heterakis and Capillaria in poultry and in swine. Fenbendazole is often administered in the feed, or in the case of poultry and swine, in the drinking water.

Fenbendazole is insoluble in water. The aqueous suspensions of the compound have been unsatisfactory because the compound does not stay in suspension. Accordingly, there remains a need for stable aqueous suspensions of fenbendazole.

Thus, it is an object of the present invention to provide for stable, efficacious aqueous formulations of fenbendazole.

It is further an objective of this invention to provide aqueous suspensions of fenbendazole wherein there is no agglomeration of particles or change in particle size after the suspension has been stored for a period of time.

The instant invention provides an aqueous formulation of fenbendazole which is stable and efficacious, does not agglomerate upon standing and wherein the fenbendazole remains in suspension after standing for twenty-four hours.

More particularly, the formulation comprises a therapeutically effective amount of fenbendazole, a preservative, surfactant and water. Preferably the preservative is an arylalkyl alcohol such as benzyl alcohol. Preferably the surfactant is a polysorbate such as polyoxyethylene (20) sorbitan monoleate.

The fenbendazole is present in the formulation in an amount from about 10% to about 30% by weight, preferably from about 15% to about 25%, most preferably about 20% by weight.

The preservative is one known to those in the art, preferably benzyl alcohol. It is present in an amount from about 1% to about 3% by weight, preferably from about 1.5% to about 2.5%, most preferably about 2% by weight.

The surfactant is preferably a water soluble nonionic surface active agent comprised of complex esters and esterethers derived from hexahydric alcohols, alkylene oxides and fatty acids by adding polyoxyethylene chains to hydroxyl of sorbitol and hexitrol anhydrides (hexitans and hexides) derived from sorbitol and then partially esterifying with the common fatty acids such as lauric, palmitic, stearic and olenic. Preferably these are the Tween type products known in the art. Most preferably the surfactant is Tween 80, known in the pharmaceutical industry as Polysorbate 80, having the chemical name is polyoxyethylene (20) sorbitan monooleate. The surfactant is present in the formulation at from about 5% to about 15% by weight, preferably from about 7.5% to about 12.5% by weight, most preferably about 10%.

Any type of water may be used in the formulation, for example, deionized water or hard water.

Optionally, the formulation may also contain an antifoaming agent, such as for example, simethicone emulsion USP. The antifoaming agent is present in sufficient concentration to allow control of the foam which forms when the formulation of the instant invention is diluted with water. In the instant invention the simethicone may be present at concentration of from about 0.2% by weight to about 1% by weight, preferably about 0.5% by weight.

In another embodiment of this invention the concentrated (about 10% to about 30% fenbendazole) formulation is diluted with water to yield a formulation where the fenbendazole is present in a concentration in the range of from about 4,000 ppm to about 10,000 ppm, preferably from about 6,000 ppm to about 10,000 ppm, most preferably about 8,000 ppm. This formulation is used to treat poultry with fenbendazole in the drinking water. The diluted formulation is used in a proportioner or medicator as is known in the art. The medicator uses for example 1 oz of the stock formulation and further dilutes with water generally in about a 1:128 ratio to obtain medicated drinking water having a fenbendazole concentration of from about 45 to about 80 ppm, preferably about 65 ppm. Alternatively, the "20%" formulation is diluted directly to a concentration of from about 45 ppm to about 80 ppm, preferably about 65 ppm and used for poultry drinking water directly.

The concentration of the fenbendazole is calculated to provide the targeted amount of fenbendazole per body weight (BW) of the poultry being treated, preferably in the range of about 1 mg to about 5 mg of fenbendazole per kilogram of body weight per day in the volume of drinking water normally consumed by the poultry being treated in a 6 to 12 hour treatment period. The targeted dosage is dictated by the parasitic species infection being treated and is known in the art.

The medicated drinking water is used to treat the poultry for about 6 to about 12 hour treatment periods, preferably about 8 hour treatment periods on each of two to six consecutive days.

Of course, to treat swine the concentrated solution is diluted to achieve the desired concentration so as to obtain drinking water containing an efficacious amount of fenbendazole to control helminths in swine. The efficacious amount is dependent on the helminth species infection being treated and is known in the art.

The concentrated formulation of the invention is typically prepared by adding the preservative and surfactant to the water and stirring until dissolved. The fenbendazole is then added and the mixture is stirred until it is homogeneous.

The mixture is then passed through a homogenizer to obtain relatively uniform particle size distribution on the order of about 1 micron (m). The homogenization is carried out by means known in the art such as for example with a rotor stator or a high pressure homogenizer. When using a single head high pressure homogenizer, the mixture is passed through until the pressure can be maintained within the range of from 9,000 to about 15,000 psig, preferably in a range of from about 12,000 psig to about 14,000 psig, most preferably within a range of about 13,000 psig. When using a triple head high pressure homogenizer, the mixture is passed through at a pressure of from about 2,000 psig to about 10,000 psig, preferably within a range of from about 4,000 psig to about 8,000 psig.

The following non-limiting examples are provided to illustrate the methods of preparation of compositions both within and without the compositions of this invention.

EXAMPLE 1

To 1,300 ml of purified water, USP, there was added 40 grams (g) of benzyl alcohol and 200 g of polysorbate 80 and the mixture was stirred until a complete solution was formed. Then there was added 400 g of fenbendazole and the mixture was stirred until it was homogeneous. Sufficient water was added to bring the total volume to 2,000 ml. Then the mixture was passed twice through a Rannie high pressure homogenizer (Model MINI-LAB, type 8.30 H). During the initial pass through the pressure fluctuated greatly. On the second pass the pressure was maintained between 12,000 psig and 13,000 psig.

EXAMPLE 2

To 1,300 ml of purified water, USP, there was added 40 g of benzyl alcohol and 200 g of Poloxamer 188 (an α-hydro-ω-hydroxypoly(oxyetheylene)poly-(oxypropylene)poly-(oxyethylene) block copolymer) and the mixture was stirred until a complete solution was formed. Then there was added 400 g of fenbendazole and the mixture was stirred until it was homogeneous. Sufficient water was added to bring the total volume to 2,000 ml. Then the mixture was passed twice through a Rannie high pressure homogenizer (Model MINI-LAB, type 8.30 H), first at 8,000 to 10,000 psig and then at 13,500 psig.

The formulations of the invention were evaluated as follows:

One drop of suspension was placed in 10 ml of water and the samples were shaken on an Eberbach shaker for 1 minute and then removed. The samples were then stored at −10° C., room temperature and 55° C. for three months and then examined for viscosity and particle size. Additionally, the samples were examined at 24 hours to see if the particles were still in suspension. The results for Examples 1 and 2 are set forth in Table 1.

TABLE 1

| Example No. | Temperature °C. | Viscosity | Particle Size | Suspension after 24 Hours |
|---|---|---|---|---|
| 1 | RT | Low | Normal | YES |
|   | 55 | Low | Normal | YES |
|   | −10 | Low | Normal | YES |
| 2 | RT | Low | Normal | NO |
|   | 55 | Low | Normal | NO |
|   | −10 | Low | Normal | NO |

EXAMPLE 3

To 3,750 ml of purified water, USP there was added 1,000 g of Polysorbate 80, NF and 50 g of simethicone emulsion, USP and the mixture was stirred until it was homogeneous. Then there was added 200 g of benzyl alcohol, NF and 2,000 g of fenbendazole and the mixture was stirred until it was homogeneous, following which an additional 4,097.5 ml of purified water, USP was added while mixing. Mixing was continued until the mixture was homogeneous.

The suspension was divided into 7 portions, A through G. Portions B to G were homogenized each using a different homogenizer or different processing conditions. The viscosity of each portion was measured with a Brookfiled viscometer model RVTI, Spindle HRVI, speed 5 rpm. In addition the particle size distribution was determined by the Galai Cl S-1 automated particle size analyzer with a 1° wedge prism installed in the 0–60 M range. Each sample was analyzed four times and the results were averaged. The processing conditions for each sample are set forth in Table 2 along with the viscosity data for each portion.

TABLE 2

| Sample | Processing | Viscosity |
|---|---|---|
| A | No Additional Processing | 40 cps |
| B | Arde-Barinco 30 minutes at setting 25 | 34 cps |
| C | Union Homogenizer HTD1 1 pass at 2,000 psi | 50 cps |
| D | Union Homogenizer HTD1 1 pass at 4,000 psi | 60 cps |
| E | Union Homogenizer HTD1 1 passs at 6,000 psi | 70 cps |
| F | Union Homogenizer HTD1 1 pass at 8,000 psi | 96 cps |
| G | Union Homogenizer HTD1 2 passes at 8,000 psi | 126 cps |

It is to be understood that changes and variations may be made without departing from the spirit and scope of the invention as defined by the appended claims.

I claim:

1. An aqueous composition for oral administration which comprises a therapeutically effective amount of fenbendazole, a preservative, a surfactant and water; wherein the fenbendazole remains in suspension after twenty-four hours and the fenbendazole particles do not agglomerate upon standing for about three months.

2. The composition of claim 1 wherein the surfactant is a polysorbate.

3. The composition of claim 2 wherein the preservative is an arylalkyl alcohol.

4. The composition of claim 3 wherein the surfactant is polyoxyethylene (20) sorbitan monooleate.

5. The composition of claim 4 wherein the preservative is benzyl alcohol.

6. A aqueous composition which comprises a therapeutically effective amount of fenbendazole, a preservative, a surfactant and water; wherein the fenbendazole remains in suspension after twenty-four hours and the fenbendazole particles do not agglomerate upon standing for about three months and wherein the fenbendazole is present in an amount of from about 10% to about 30% by weight, the preservative is present in an amount of from about 1% to about 3% by weight, and the surfactant is present in an amount of from about 5% to about 15% by weight.

7. The composition of claim 6 wherein the fenbendazole is present in an amount of from about 15% to about 25% by weight, the preservative is present in an amount of from about 1.5% to about 2.5% by weight, and the surfactant is present in an amount of from about 7.5% to about 12.5% by weight.

8. The composition of claim 7 wherein the fenbendazole is present in an amount of about 20% by weight, the preservative is present in an amount of about 2% by weight, and the surfactant is present in an amount of about 10% by weight.

9. The composition of claim 6 wherein the surfactant is a polysorbate.

10. The composition of claim 9 wherein the preservative is an arylalkyl alcohol.

11. The composition of claim 10 wherein the surfactant is polyoxyethylene (20) sorbitan monooleate.

12. The composition of claim 11 wherein the preservative is benzyl alcohol.

13. An aqueous composition which comprises a therapeutically effective amount of fenbendazole, a preservative, a surfactant and water; wherein the fenbendazole remains in suspension after twenty-four hours and the fenbendazole particles do not agglomerate upon standing for about three months; and wherein the fenbendazole is present in an amount of from about 4,000 ppm to about 12,000 ppm be weight, the preservative is present in an amount of from about 400 ppm to about 1200 ppm by weight, and the surfactant is present in an amount of from about 2,000 ppm to about 6,000 ppm by weight.

14. The composition of claim 13 wherein the fenbendazole is present in an amount of from about 6,000 ppm to about 10,000 ppm by weight, the preservative is present in an amount of from about 600 ppm to about 1,000 by weight, and the surfactant is present in an amount of from about 3,000 ppm to about 5,000 ppm by weight.

15. The composition of claim 14 wherein the fenbendazole is present in an amount of about 8,000 ppm by weight, the preservative is present in an amount of about 500 ppm by weight, and the surfactant is present in an amount of about 4,000 ppm by weight.

16. The composition of claim 13 wherein the surfactant is a polysorbate.

17. The composition of claim 16 wherein the preservative is an arylalkyl alcohol.

18. The composition of claim 17 wherein the surfactant is polyoxyethylene (20) sorbitan monooleate.

19. The composition of claim 18 wherein the preservative is benzyl alcohol.

20. An aqueous composition which comprises a therapeutically effective amount of fenbendazole, a preservative, a surfactant and water; wherein the fenbendazole remains in suspension after twenty-four hours and the fenbendazole particles do not agglomerate upon standing for about three months; and wherein the fenbendazole is present in an amount from about 45 ppm to about 80 ppm by weight, the preservatives is present in an amount of from about 4.5 ppm to about 8 ppm by weight, and the surfactant is present in an amount of from about 25 ppm to about 40 ppm by weight.

21. The composition of claim 20 wherein the fenbendazole is present in an amount of about 6.5 ppm by weight, the preservative is present in an amount of about 6.5 ppm by weight, and the surfactant is present in an amount of about 32.5 ppm by weight.

22. The composition of claim 21 wherein the surfactant is a polysorbate.

23. The composition of claim 22 wherein the preservative is an arylalkyl alcohol.

24. The composition of claim 23 wherein the surfactant is polyoxyethylene (20) sorbitan monooleate.

25. The composition of claim 24 wherein the preservative is benzyl alcohol.

26. The composition of claim 1 which additionally comprises an antifoaming agent.

27. The composition of claim 26 wherein the antifoaming agent is simethecone emulsion USP.

28. The composition of claim 6 which additionally comprises an antifoaming agent.

29. The composition of claim 28 wherein the antifoaming agent is simethecone emulsion USP.

30. The composition of claim 13 which additionally comprises an antifoaming agent.

31. The composition of claim 30 wherein the antifoaming agent is simethecone emulsion USP.

32. The composition of claim 20 which additionally comprises an antifoaming agent.

33. The composition of claim 32 wherein the antifoaming agent is simethecone emulsion USP.

* * * * *